Figure 1:
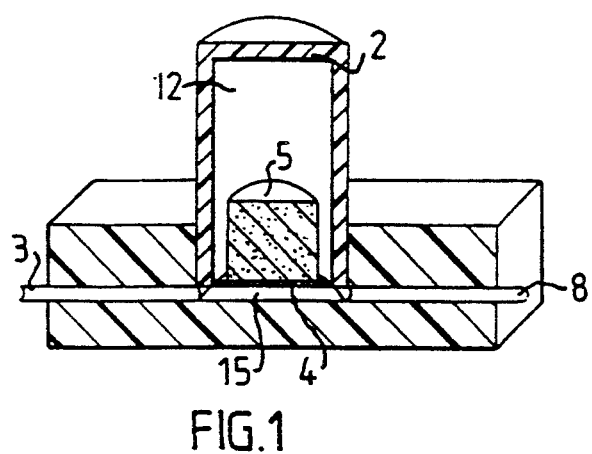

United States Patent [19]
Berglund

[11] Patent Number: 5,395,323
[45] Date of Patent: Mar. 7, 1995

[54] DISSOLUTION SYSTEM

[75] Inventor: Bengt G. Berglund, Göteborg, Sweden

[73] Assignee: Aktiebolaget Astra, Sodertalje, Sweden

[21] Appl. No.: 848,959

[22] PCT Filed: Oct. 26, 1990

[86] PCT No.: PCT/SE90/00698

§ 371 Date: Apr. 21, 1992

§ 102(e) Date: Apr. 21, 1992

[87] PCT Pub. No.: WO91/06330

PCT Pub. Date: May 16, 1991

[30] Foreign Application Priority Data

Oct. 26, 1989 [SE] Sweden ................... 8903563

[51] Int. Cl.6 ............................................ A61M 37/00
[52] U.S. Cl. .................................................... 604/84
[58] Field of Search ................................ 604/80-85, 604/91, 90, 92, 56

[56] References Cited

U.S. PATENT DOCUMENTS

| | | | |
|---|---|---|---|
| 4,511,352 | 4/1985 | Theeuwes et al. | 604/85 |
| 4,623,334 | 11/1986 | Riddell | 604/85 |
| 4,681,582 | 7/1987 | Yamameto | 604/84 |
| 4,740,200 | 4/1988 | Theeuwes | 604/85 |
| 4,855,064 | 8/1989 | Schlein | 604/83 |
| 4,874,366 | 10/1989 | Zdeb et al. | 604/85 |

*Primary Examiner*—C. Fred Rosenbaum
*Assistant Examiner*—Manuel Mendez
*Attorney, Agent, or Firm*—White & Case

[57] ABSTRACT

The invention provides a device for mixing a pharmaceutical from a solid supply into a parenterally acceptable liquid flowing through a set for parenteral administration of the liquid to a patient, said device comprising a first compartment defining a mixing space through which the liquid flows in a define flow direction and in which the liquid mixes with the pharmaceutical in liquid solution. The device is characterized in said mixing space being limited in an upper part thereof by a generally horizontal partition parallel to the flow direction in the mixing space and a second compartment extending generally vertically above said partition and being in liquid communication with the mixing space via perforations in said partition, said second compartment being closed and gas impervious in its upper end and defining a space for dissolution of the pharmaceutical in liquid penetrating through the perforations, and said second compartment further comprising a storage space where undissolved solid pharmaceutical is held surrounded by entrapped gas.

6 Claims, 4 Drawing Sheets

DISSOLUTION SYSTEM

The present invention is related to a novel system for dissolution of a solid compound to a parenteral flow of liquid.

An object of the invention is to achieve a device for administration of a drug which is unstable in solution to said parenteral flow of liquid.

Devices for dissolution of a solid compound to a parenteral liquid are known in the art. Thus, EP 0059694 (Hässle), EP 0077604 (Eli Lilly), U.S. Pat. No. 4,534,758 (Eli Lilly), EP 0100296 (Ciba-Geigy), EP 85850141.4 (Hässle) and WO 86/03416 (Baxter Travenol) and WO 86/03417 (Baxter Travenol) all describe such devices. In all of the above mentioned devices the drug is completely surrounded by the liquid, either as a drug formulation (e.g. a plain tablet, a coated tablet or a matrix tablet) or as a powder behind a membrane. In the case of the powder, the chamber behind the membrane is provided with an air-venting filter, thus allowing the entrapped air to escape and the powder is then completely surrounded by liquid.

Devices for release of a solid compound into a non-parenteral liquid are described in U.S. Pat. Nos. 3,390,695 and 3,474,817.

DISCLOSURE OF THE INVENTION

The invention provides a device for mixing a pharmaceutical from a solid supply into a parenterally acceptable liquid flowing through a set for parenteral administration of the liquid to a patient, said device comprising a first compartment defining a mixing space through which the liquid flows in a defined flow direction and in which the liquid mixes with the pharmaceutical in liquid solution, and the device is characterized in said mixing space being limited in an upper part thereof, by a generally horizontal partition parallel to the flow direction in the mixing space, and a second compartment extending generally vertically above said partition and being in liquid communication with the mixing space via perforations in said partition, said second compartment being closed and gas impervious in its upper end and defining a space for dissolution of the pharmaceutical in liquid penetrating trough the perforations, and said second compartment further comprising a storage space where undissolved solid pharmaceutical is held surrounded by entrapped gas.

According to one embodiment of the invention the device consists of a vertically orientated container which is impermeable to air except for its lower end which is covered by a support (screen or membrane). The drug is resting on the support and can be formulated either as a tablet or as a powder. The liquid is allowed to flow by under the support and a force (e.g. gravitation or a spring) brings the compound in contact with the liquid. Due to the impermeability of the container walls, no air can escape from the container and thus no or a very small volume of liquid enters the container.

Figure 5:
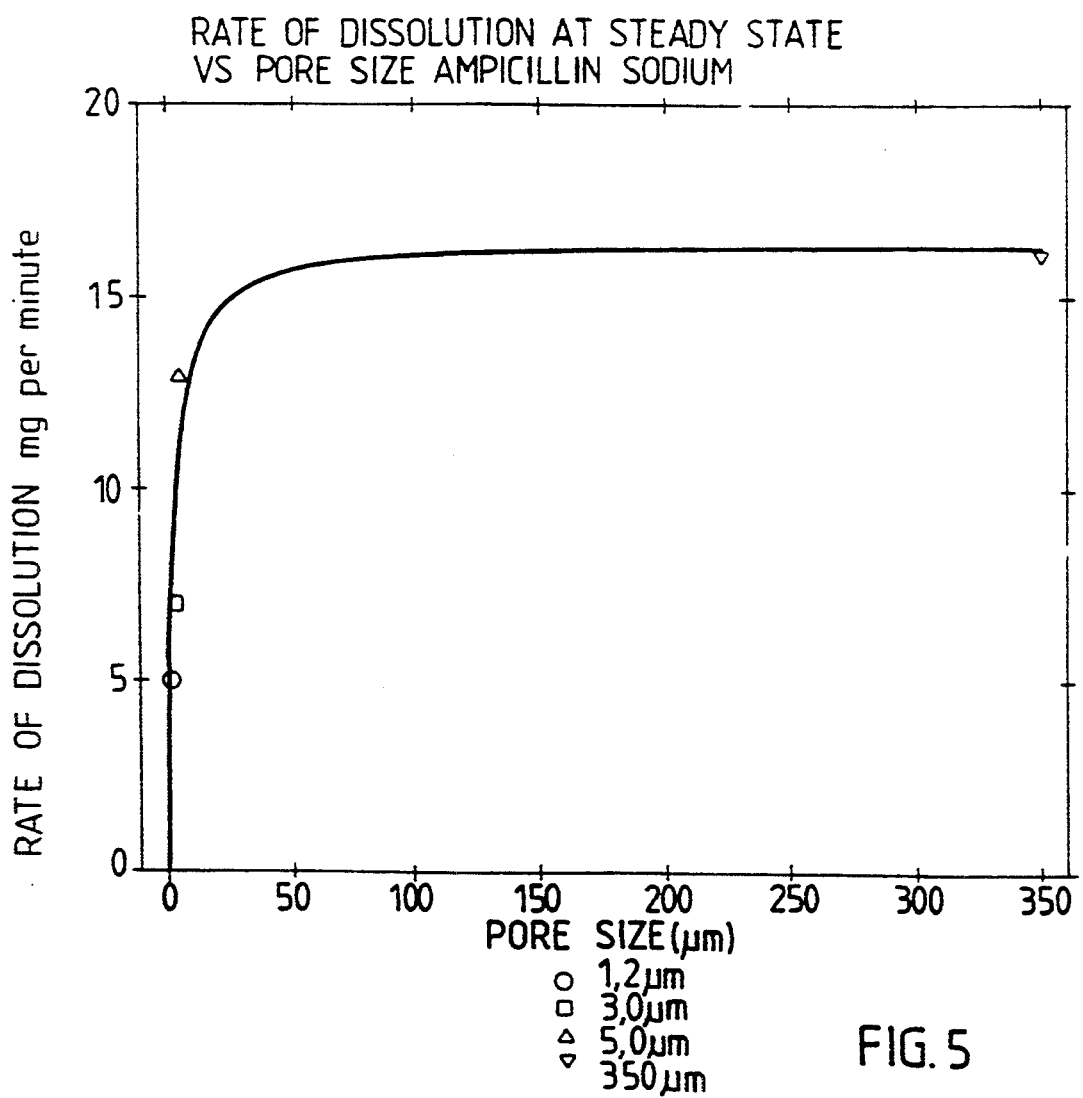
Figure 4:
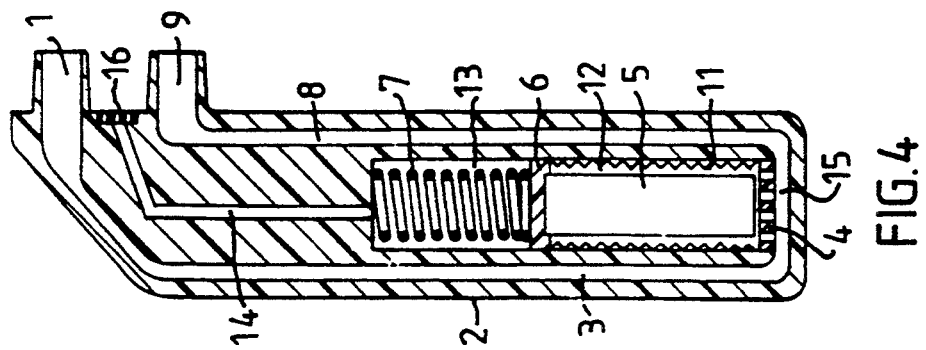
Figure 3:
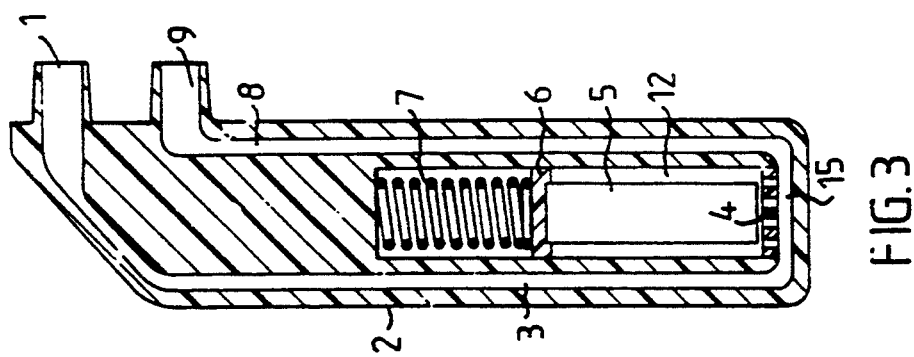
Figure 2:
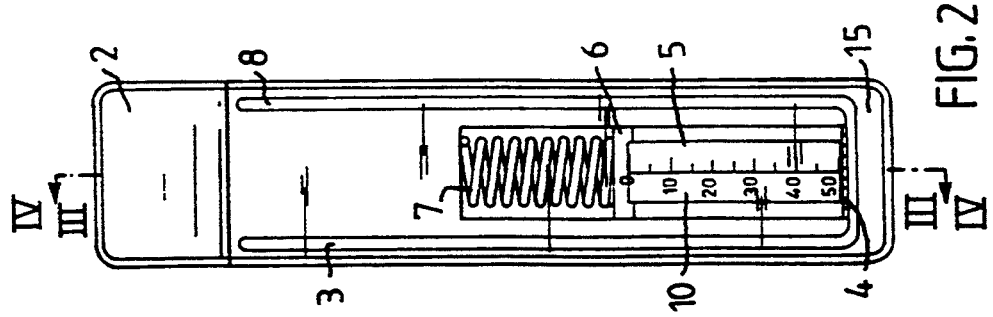
Figure 6:
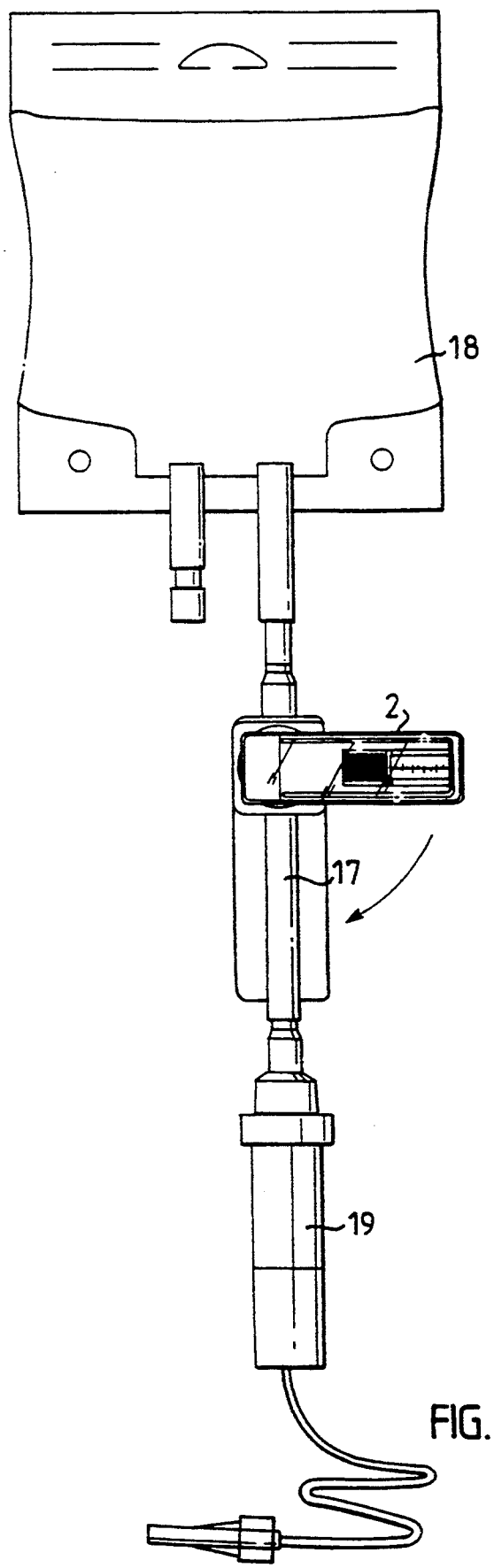
Figure 7:
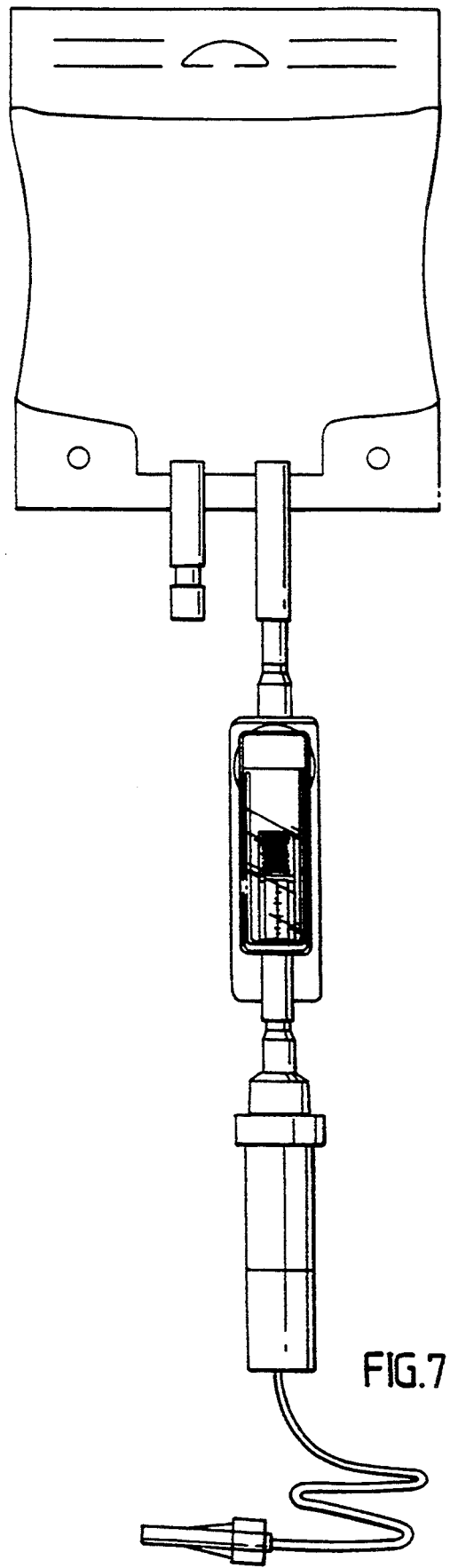

The invention is further described with reference to the enclosed drawings, wherein FIG. 1 is a schematic section through a device according to the present invention, FIG. 2 is a view of a device according to one embodiment of the present invention wherein the device is shown partly transparent to disclose inner parts thereof, FIG. 3 is a section through the device in FIG. 2 along the line A—A, FIG. 4 is a section through another device in accordance with FIG. 2 along the line A—A, FIG. 5 is a diagram of rate of dissolution as a function of pore size in a device according to the invention, FIG. 6 is a view if an infusion set incorporating the device of the invention, wherein the device of the invention is shown in a closed position, and FIG. 7 is a view of the infusion set of FIG. 6 wherein the device of the invention is shown in an open position.

Figure 8:
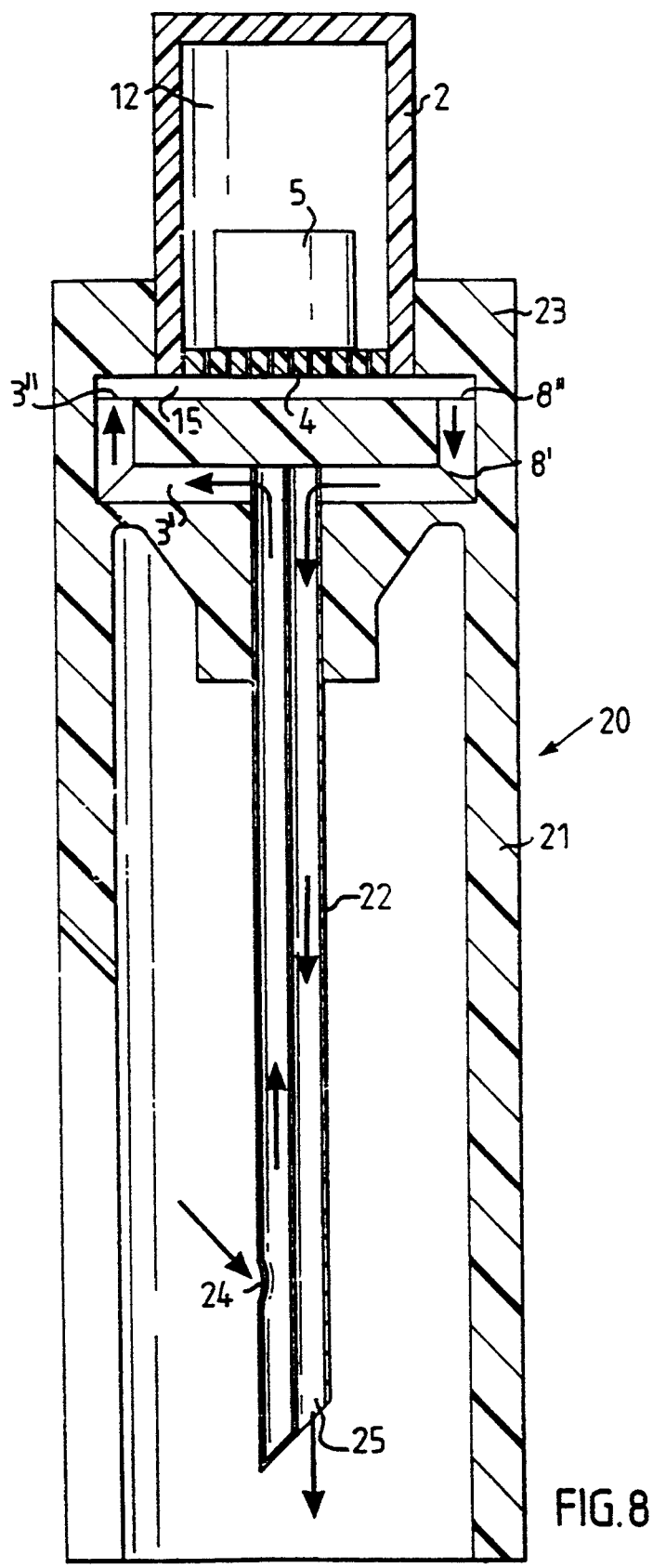

FIG. 8 is a section through a device according to a further embodiment of the present invention.

In the embodiment shown in FIG. 1 a suitable liquid for parenteral use is entered through an inlet channel 3 and transported to a first compartment or mixing space 15. A drug formulation 5 (e.g. a tablet) is placed in a second compartment or chamber 12 defined by a container 2 and separated from the mixing space by a screen 4. Only the lower part of the drug formulation will be in contact with the liquid. The drug will be dissolved from below and mixed with the infusion livid. After leaving the device through outlet channel 8 the drug solution will finally be entered into a patient's vein. The remaining part of the drug formulation is dry and continuously falls to the lower part of the chamber and thus brings new dry drug in contact with the liquid for dissolution. In this device the air is not to be removed from the chamber 12. The presence of air surrounding the drug preparation means that it is possible to administer drugs which have poor stability in solution by a parenteral route.

Another embodiment of the invention is shown in FIGS. 2 and 3. The embodiment shown in FIG. 2 is intended to function as a drug container to be connected to a connector 17 shown in FIG. 6, said connector being interposed between an infusion bag 18 and an infusion set 19. The above mentioned connector and drug container are described in WO 88/00476. The open (working) position of the drug container is vertical as shown in FIG. 7.

A suitable parenteral liquid is entered through inlet socket 1 of the container 2. The liquid is transported through inlet channel 3 to the mixing space 15. The drug formulation 5 in the compound compartment 12 will be in liquid communication with the fluid through a screen 4. To keep the drug formulation in position a spring 7 and guiding cap 6 is used. As the drug formulation continuously dissolves and is transported away through outlet channel 8 and outlet socket 9, the guiding cap will move down and the position of the guiding cap on the scale 10 will show the amount of drug dissolved. Thus, another advantage compared to the previously mentioned devices is that this invention makes it possible to visually see how much of the dose that has been administered to the patient.

If the solid compound consists of a very large dose (>1 g) the volume of liquid entering the chamber can not be negligible. The chamber inside the container contains air and the solid compound. When the solid compound is dissolved and transported away it has to be replaced with something else and this will naturally be the liquid. Thus, the level of liquid will rise in the chamber. To avoid this, the device can be equipped with a bellows folded wall sealed between the guiding cap 6 and the screen 4 limiting the compartment 12 from a spring compartment 13, as in yet another embodiment shown in FIG. 4. Thus, when the tablet dissolves from below, it gets shorter and the spring compresses the bellows folded wall 11 reducing the volume of the compartment therein, and the device is compensated for the volume of the lost compound. Air has to be entered to the spring compartment 13 through a filter 16 and an air channel 14. The level of the liquid will not rise and the remaining solid compound is dry.

In FIG. 8 the device is designed similar to the cartridge shown in FIGS. 16 and 17 of WO 86/03416, the description of which figures is incorporated by reference herein. In FIG. 8, cartridge 20 is designed to fit on a receptacle in-line in a parenteral liquid-administration system as shown in FIG. 16 of WO 86/03416. It comprises a sleeve 21 covering a double-lumen needle 22 adapted for piercing or otherwise entering the receptacle via a pierceable or otherwise unsealable and resealable entrance situs thereon, and an upper part 23 containing in essence the schematically shown device of FIG. 1. The liquid is entered into the device via an inlet opening 24 in the needle and flows throw one lumen in the needle to exit the same into an inlet channel 3', which is similar to inlet channel 3 except for being divided in two sections at right angles to each other, and for entering the mixing space 15 from a peripheral bottom inlet opening 3" therein. The container 2, screen 4, drug formulation 5 and chamber 12 functions as indicated with FIG. 1, while outlet channel 8' is similar to outlet channel 8 except for being divided in two sections at right angles to each other, and for leaving the mixing space 15 through a peripheral bottom outlet opening 8" therein. The liquid exits the device via the second lumen of the needle via a distal outlet opening 25.

In the device of the invention the rate of dissolution is dependent on the area of the support (and the tablet). The greater the area the higher the rate of dissolution. It is however possible to modify the rate of dissolution by mixing the active substance with a non-active water-soluble substance (e.g. polyethyleneglycol) and thus reach a lower rate of dissolution. The rate of dissolution is also dependent on the pore size of the support. The smaller the pore size the lower the rate of dissolution.

EXAMPLE 1

750 mg of ampicillin sodium was compressed to a tablet in a single punch press. The diameter of the tablets were 8 mm and the height 13.9 mm. The tablet was placed in a device according to FIG. 1. The pore size of the support screen was 350 μm, the diameter of the container was 12 mm and the height 15 mm. A liquid consisting of normal saline was allowed to flow by the support screen with a flow rate of 200 ml/h and the amount of ampicillin sodium in the efflux was measured continuously by UV-detection. The rate of release and the cumulated amount released are shown in Table 1. When 375 mg of ampicillin sodium had been dissolved and transported away the tablet height had been reduced to 7 mm and when all of the substance had been dissolved and transported away, naturally, there was no visible tablet left. It is obvious that it is easy to change the duration of the formulation by simply modifying the height of the tablet. The higher the tablet the longer the duration, but the rate of release will be the same. This is because the bottom areas of the two formulations are the same.

TABLE 1

| Time min | Release rate mg/min | Cumulated amount released % |
|---|---|---|
| 0 | 0 | 0 |
| 5 | 16.3 | 10.3 |
| 10 | 15.7 | 18.9 |
| 15 | 14.8 | 31.0 |
| 20 | 15.5 | 40.9 |
| 25 | 14.7 | 51.2 |
| 30 | 15.7 | 61.3 |
| 35 | 17.1 | 72.4 |
| 40 | 14.9 | 83.5 |
| 45 | 13.5 | 93.7 |
| 50 | 2.3 | 99.5 |
| 55 | 0.1 | 99.9 |
| 60 | 0 | 100 |

To investigate the importance of the pore size, the above mentioned experiment was carried out with filter membranes having pore sizes of 1.2, 3.0 and 5.0 μm respectively. The dissolution rate at steady state was measured. As can be seen in FIG. 5 of the rate of dissolution is dependent on the pore size. At small pore sizes (<50 μm) there is little circulation and mainly diffusion of liquid through the membrane. At larger pore sizes (>50 μm) there is mainly liquid circulation through the membrane.

The larger pore sizes are mainly useful when the drug formulation is a tablet and the dissolution rate is dependent on the hardness of the tablet (and the area). Consequently, the smaller pore sizes are useful when the drug formulation is a powder. The smaller pore size retain the powder in the container and the dissolution rate is dependent on the pore size.

EXAMPLE 2

46 mg of omeprazole sodium was compressed to a tablet in a single punch press. The diameter of the tablets were 8 mm and the height 1 mm. The tablets was placed in a device according to FIG. 1. The pore size of the support screen was 120 μm, the diameter of the container was 9 mm and the height 10 mm. A liquid consisting of normal saline was allowed to flow by the support screen with a flow rate of 200 ml/h and the amount of omeprazole sodium in the efflux was measured continuously by UV-detection. The rate of release and cumulated amount released are shown in table 2. This shows a profile suitable for a drug to be administered parenterally over a time period of 20–30 minutes.

TABLE 2

| Time min | Release rate mg/min | Cumulated amount released % |
|---|---|---|
| 0 | 0 | 0 |
| 1 | 4.1 | 6.4 |
| 2 | 4.1 | 15.8 |
| 4 | 3.9 | 33.4 |
| 6 | 3.6 | 49.9 |
| 8 | 3.3 | 65.1 |
| 10 | 2.9 | 78.7 |
| 12 | 2.1 | 89.4 |
| 14 | 0.9 | 96.0 |
| 16 | 0.4 | 98.4 |
| 18 | 0.1 | 99.3 |
| 20 | 0.04 | 99.7 |

I claim:

1. A device for mixing a pharmaceutical, in a solid form, into a parenteral fluid flowing though a parenteral fluid system, said device comprising:

a first compartment defining a mixing space;

inlet and outlet means for directing fluid though said mixing space in a defined flow direction, for mixing with the pharmaceutical;

a perforated partition defining an upper portion of said mixing chamber and being oriented generally parallel to the fluid flow direction;

a second compartment for containing a solid pharmaceutical and a gas, said second compartment having a first end in fluid communication with said first compartment through said partition, said second compartment including means for urging the pharmaceutical against said partition, and having a second end which is closed and gas impervious such that, in use, fluid penetrates said perforations only into a portion of said second compartment adjacent said partition, for dissolving the pharmaceutical adjacent to the partition, but the remaining part of the pharmaceutical remains surrounded by gas.

2. A device according to claim 1 wherein the partition is generally horizontal, the second compartment is located generally vertically above said partition, and the means for urging the pharmaceutical against the partition is gravity.

3. A device according to claim 1, wherein the partition is generally horizontal, the second compartment is located generally vertically above said partition, and the means for urging the pharmaceutical against the partition comprises spring means disposed in said second compartment for urging said pharmaceutical towards said partition.

4. A device according to claim 3, wherein the second end of said second compartment is movable toward said partition, wherein said spring means acts on said second end for urging said second end and pharmaceutical toward said partition, and said second compartment further comprises means for forming a seal between the second end and said partition.

5. A device according to claim 3 further comprising bellows means for sealing the pharmaceutical from the fluid.

6. A device according to claim 1, further comprising a double-lumen needle of the type that is designed to fit on a receptacle in-line in a parenteral administrative system, means for connecting one lumen of said double lumen needle to said inlet means, and means for connecting said outlet means to the other lumen of said double lumen, whereby parenteral fluid may flow from said one lumen to said mixing space, and thereafter through said other lumen.

* * * * *